United States Patent
Kura et al.

(10) Patent No.: US 6,712,756 B1
(45) Date of Patent: *Mar. 30, 2004

(54) ENDOSCOPE SYSTEM HAVING TRANSPONDER FOR DISCRIMINATING ENDOSCOPE

(75) Inventors: Yasuhito Kura, Hachioji (JP); Tetsuaki Mori, Huntington Station, NY (US)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 140 days.

(21) Appl. No.: 09/634,251

(22) Filed: Aug. 7, 2000

(30) Foreign Application Priority Data

May 19, 2000 (JP) ........................................ 2000-148060

(51) Int. Cl.⁷ ................................................ A61B 1/00
(52) U.S. Cl. ........................ 600/118; 600/133; 600/117
(58) Field of Search ................................ 600/117, 118, 600/103, 133, 109

(56) References Cited

U.S. PATENT DOCUMENTS

| | | |
|---|---|---|
| 4,862,872 A | 9/1989 | Yabe et al. |
| 4,996,975 A | 3/1991 | Nakamura |
| 5,535,141 A | 7/1996 | Lüssi |
| 5,732,401 A * | 3/1998 | Conway .................... 700/90 |
| 5,830,121 A | 11/1998 | Endomoto et al. |
| 5,871,439 A * | 2/1999 | Takahashi et al. ............ 348/74 |
| 5,899,852 A * | 5/1999 | Takahashi et al. .......... 600/118 |
| 5,967,969 A | 10/1999 | Enomoto et al. |
| 6,092,722 A * | 7/2000 | Heinrichs et al. ........... 235/375 |
| 6,356,780 B1 * | 3/2002 | Licato et al. ............... 382/128 |
| 6,366,206 B1 * | 4/2002 | Ishikawa et al. ......... 340/572.1 |
| 6,436,032 B1 * | 8/2002 | Eto et al. .................... 600/117 |

FOREIGN PATENT DOCUMENTS

| | | |
|---|---|---|
| DE | 195 14 284 A | 10/1996 |
| DE | 197 23 442 A | 2/1998 |
| EP | 0 945 140 A | 9/1999 |

* cited by examiner

Primary Examiner—John P. Leubecker
(74) Attorney, Agent, or Firm—Frishauf, Holtz, Goodman & Chick, P.C.

(57) ABSTRACT

An endoscope system has at least one of an endoscope including a first discrimination section having readable characteristic information for discriminating each endoscope, a peripheral device including a second discrimination section having readable characteristic information for discriminating each peripheral device, and a third discrimination section having readable characteristic information for discriminating an operator operating the endoscope or the peripheral device. A reading section is capable of reading the characteristic information of the first, second or third discrimination section. A management section manages a status of use of the endoscope and information related to the peripheral device and the endoscope.

15 Claims, 6 Drawing Sheets

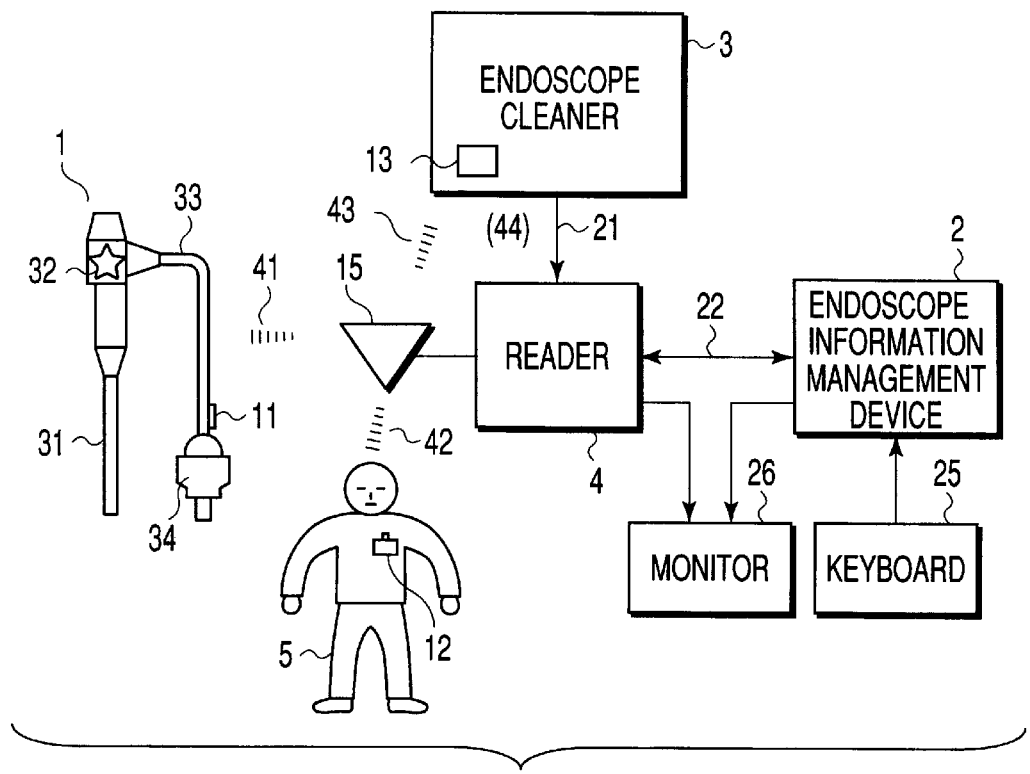

FIG. 1

44 ~
- CLEANING / DISINFECTION DATE (YEAR,MONTH,DAY)
- SELECTED CLEANING / DISINFECTION STEP
- WATER LEAKAGE INSPECTION START TIME (HOUR,MINUTE,SECOND)
- CLEANING START TIME (HOUR,MINUTE,SECOND)
- DISINFECTION START TIME (HOUR,MINUTE,SECOND)
- RINSE START TIME (HOUR,MINUTE,SECOND)
- DRYING START TIME (HOUR,MINUTE,SECOND)
- CLEANING / DISINFECTION TEMPERATURE
- CLEANING / DISINFECTION STEP TIME
- START TIME / FINISH TIME
- CUMULATIVE TIMES OF USING CLEANER / DISINFECTION MACHINE
- CUMULATIVE TIMES OF CLEANING ENDOSCOPE

FIG. 3

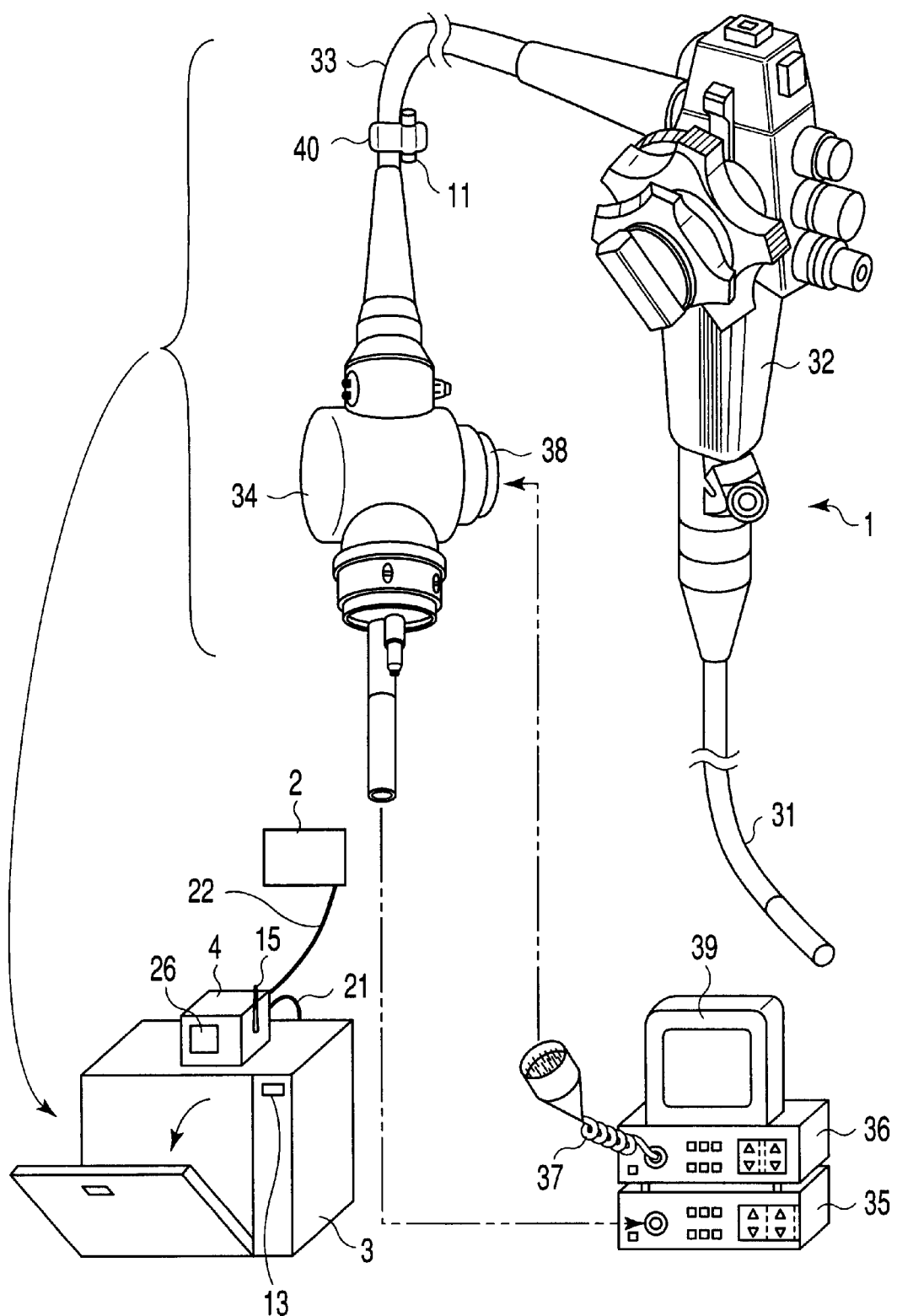
F I G. 2

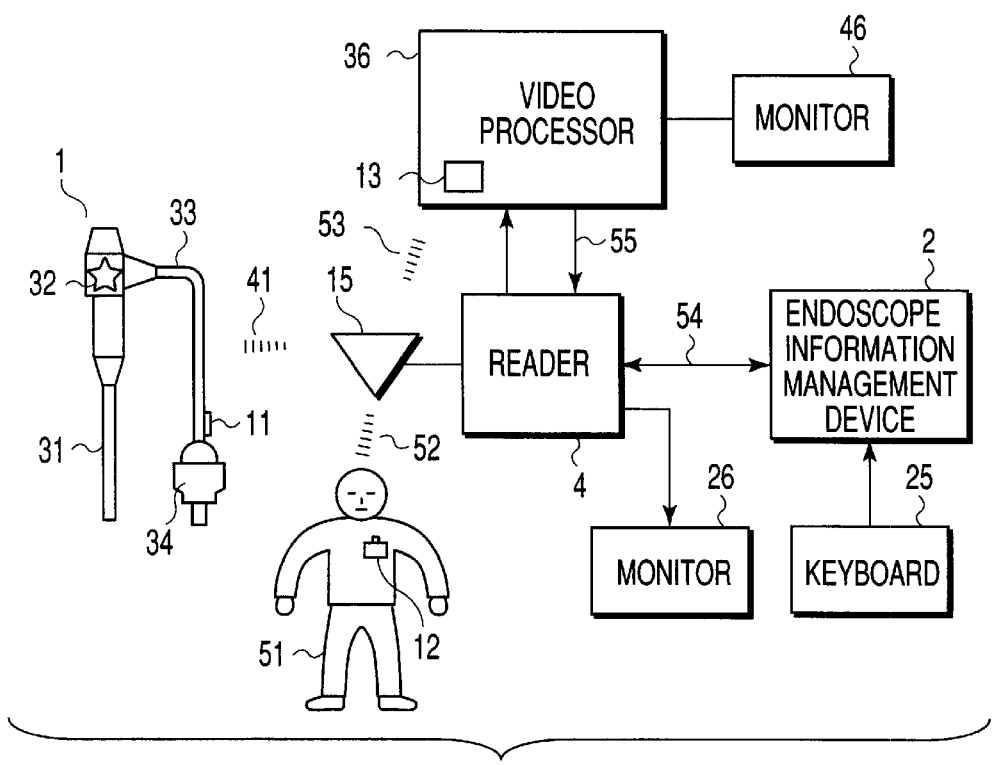
FIG. 4
FIG. 5
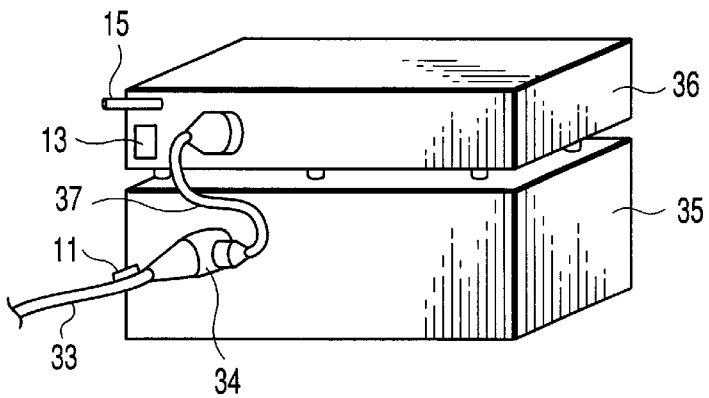
FIG. 6

ENDOSCOPE SYSTEM HAVING TRANSPONDER FOR DISCRIMINATING ENDOSCOPE

CROSS-REFERENCE TO RELATED APPLICATIONS

This application is based upon and claims the benefit of priority from the prior Japanese Patent Application No. 2000-148060, filed May 19, 2000, the entire contents of which are incorporated herein by reference.

BACKGROUND OF THE INVENTION

The present invention relates to an endoscope system consisting of endoscopes and peripherals connecting the endoscopes with one another.

When an endoscope is used, it is required to clean/disinfect the endoscope to prevent subsequent patients from being infected. For that reason, it is desirable that such an endoscope have visible cleaning information (cleaner used, cleaning/disinfection date, person who cleaned/ disinfected the endoscope, etc.).

Further, to prevent damage to an endoscope and to clarify inspection timing, it is preferable to store information such as use history (day when the endoscope was used, cumulative times of use (cleaning/disinfection), users, previous inspection/maintenance day) and the like.

Conventionally, however, a user who uses the endoscope checks and records such characteristic information.

Namely, the conventional technique has disadvantages as follows:

(1) If there are a plurality of endoscopes, it is inconvenient to discriminate and manage each of them.

(2) Even if information is managed by a computer, it is necessary to input the information every time it is required, which takes labor.

In case of cleaning/disinfecting the endoscopes between tests, in particular, it is difficult to record the above-stated information in a short time although it is desirable to make the cleaning/disinfection time as short as possible so as to conduct tests efficiently.

Further, as for an endoscope into which a memory is incorporated to store the above-stated information, if the memory is broken, the information stored therein may be damaged or lost.

BRIEF SUMMARY OF THE INVENTION

It is, therefore, an object of the present invention to provide an endoscope system capable of automatically conducting maintenance/recording of endoscope information which has been conventionally conducted by a user thereby lessening the user's burden and improving the reliability of information maintenance.

To obtain the above object, an endoscope system according to the first aspect of the present invention is characterized by comprising:

at least one of an endoscope including a first discrimination section having readable characteristic information for discriminating each endoscope, a peripheral device including a second discrimination section having readable characteristic information for discriminating each peripheral device and a third discrimination section having readable characteristic information for discriminating an operator operating the endoscope or the peripheral device;

a reading section capable of reading the characteristic information of one of the first, second and third discrimination sections; and management means for managing a status of use of the endoscope and information related to the peripheral device and the endoscope based on a reading result of the reading section.

In addition, an endoscope system according to the second aspect of the present invention is characterized by comprising:

a discrimination section provided integrally with an endoscope and having readable characteristic discrimination information for discriminating each endoscope;

a reading section reading the discrimination information on the endoscope from the discrimination section; and individual information conversion section converting the discrimination information on the endoscope read by the reading section into individual information on the endoscope.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is an overall view of an endoscope system in the first embodiment according to the present invention;

FIG. 2 is a perspective view of an endoscope, peripheral devices thereof and a cleaner in the first embodiment according to the present invention;

FIG. 3 is a data notation listing cleaning information on the endoscope system in the first embodiment according to the present invention;

FIG. 4 is an overall view of an endoscope system in the second embodiment according to the present invention;

FIG. 5 is a perspective view of a light source device and a video processor in the second embodiment according to the present invention;

FIG. 6 is a data notation listing cleaning information on the endoscope system in the second embodiment according to the present invention;

DETAILED DESCRIPTION OF THE INVENTION

First Embodiment

Figure 7:
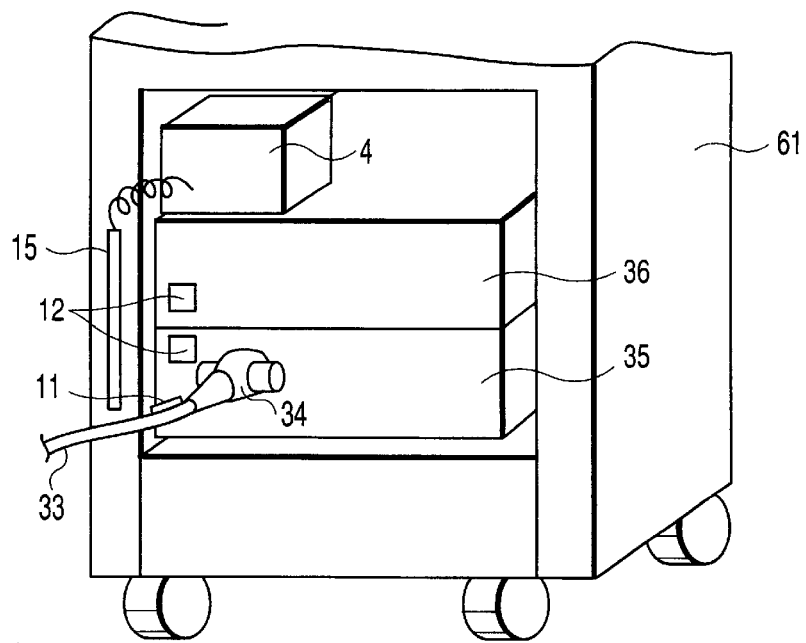
FIG. 7 is a perspective view of a light source device and a video processor contained in a trolley 61 in an endoscope system in the third embodiment according to the present invention.

The first embodiment of the present invention will be described with reference to FIGS. 1 to 3. FIG. 1 is an overall view of an endoscope system in this embodiment. FIG. 2 is a perspective view of an endoscope, peripheral devices thereof and a cleaner. FIG. 3 is a data notation listing cleaning information.

In FIG. 1, reference symbol 1 denotes an endoscope, 2 denotes an endoscope information management device, 3 denotes an endoscope cleaner (to be referred to simply as "cleaner" hereinafter) and 4 denotes a reader.

A columnar transponder 11 is attached to the endoscope 1. If there are provided a plurality of endoscopes 1, a plurality of columnar transponders 11 are attached to the respective endoscopes 1.

A user 5 holds a nameplate type transponder 12. If there are a plurality of users 5, the users 5 hold different nameplate type transponders 12, respectively. The nameplate type transponder 12 also serves as a name tag or the like and the user is supposed to always carry the transponder 12.

In addition, a nameplate type transponder 13 is detachably provided at the cleaner 3. If there are provided a plurality of cleaners 3, a plurality of different nameplates type transponders 13 are attached to the respective cleaners 3.

The columnar transponder 11 and the nameplate type transponder 12 are used in combination with an antenna 15 and the reader 4. These transponders are already commercially available, as non-contact ID systems, from, e.g., Texas Instruments, Inc. Further, each of the columnar transponder 11 and the nameplate type transponder 12 is normally referred to as a transponder, an automatic radio responder or an electric wave reflector.

In addition, the columnar transponder 11 is enclosed in a glass and is watertight. The columnar transponder 11 can be, therefore, cleaned along with the endoscope 1.

The antenna 15 is connected to the reader 4. The antenna 15 may be movably provided to be away from the reader 4 or may be fixed integrally to the reader.

The reader 4 transmits an electric wave toward the columnar transponder 11 and the nameplate type transponder 12 by way of the antenna 15, and supplies energy for response to the columnar transponder 11 and the nameplate type transponder 12. Further, the transponders 11 and 12 are applied with electric power by means of electromagnetic induction and thereby transmit recognition signals which they have, respectively. It is, therefore, unnecessary to supply power to the transponders 11 and 12, and it is possible to realize a small-sized, wireless encoder system.

Furthermore, the reader 4 is switched from a transmit state to a reception state, thereby allowing the reader 4 to receive the recognition signals by way of the antenna 15 and discriminate the transponders. Since the signal reception and transmission are conducted over electric waves, the columnar transponder 11, the nameplate type transponder 12, the antenna 15 and the reader 4 can be provided in a non-contact manner. Namely, this discrimination means and the reading means constitute a communication device employing non-contact radio transmission.

The above-stated transponders can be shaped freely such as a columnar shape, a disk shape or a cylindrical shape according to purposes. The antenna 15 can be freely set such as a pole type or a gate type according to purposes, as well.

The cleaner 3 is connected to the reader 4 by a connection cable 21. The endoscope information management device 2 is connected to the reader 4 by a connection cable 22.

The endoscope information management device 2 is provided with an input device 25 such as a keyboard or an external computer. The reader 4 is provided with a display device 26. The display device 26 is constituted to be capable of displaying information on the endoscope information management device 2.

The endoscope 1 is constituted to comprise an elongated insertion section 31 inserted into an observation target region, an operation section 32 coupled to the proximal end portion of the insertion section 31 and also serving as a grip section, a universal cord 33 including therein a signal cable extended from the sidewall portion of the operation section 32, a light guide and the like, and a connector section 34 provided on the extended tip end portion of the universal cord 33.

The endoscope 1 is detachably connected to an external light source device 35 using the connector section 34. The connector section 34 is provided with a connection section 38 for detachably connecting a connection cord 37 leading to a video processor 36.

The video processor 36 is provided with a monitor 39 for displaying observed images. In addition, a VTR deck, a video printer, a video disk, an image file recorder and the like, which are not shown, can be connected to the video processor 36.

The columnar transponder 11 is fixed to a region in the middle of the universal cord 33 by a tape-like fixing member 40.

As shown in FIG. 2, the endoscope information management device 2 is disposed on the upper surface of the main body of the cleaner 3. Accordingly, all the discrimination means of the columnar transponder 11, the nameplate transponder 12 and the nameplate type transponder 13 are provided in a state in which they are positioned adjacent to the antenna 15 of the reader 4.

Description will now be given to a case where the endoscope system is actually used. First, the following preparation is made.

(1) Registration of endoscope 1.

The columnar transponder 11 of the endoscope 1 is read by the antenna 15 and a scope identification signal 41 of the transponder 11 is transferred to the endoscope information management device 2 by way of the reader 4. Further, the input device 25, such as a keyboard or an external computer, inputs the type name and the serial number of the endoscope 1 into the endoscope information management device 2 and register individual information on the endoscope 1.

(2) Registration of user 5.

The nameplate type transponder 12 owned by the user 5 is read by the antenna 15 and a user discrimination signal 42 of the transponder 12 is transferred to the endoscope information management device 2 by way of the reader 4. Using the input device 25, individual information such as user name is registered in the endoscope information management device 2.

(3) Registration of cleaner 3.

The nameplate type transponder 13 of the cleaner 3 is read by the antenna 15 and a cleaner discrimination signal 43 of the transponder 13 is transferred to the endoscope information management device 2 by way of the reader 4. Using the input device 25, the type name and the serial number of the cleaner 3 are inputted into the endoscope information management device 2 to thereby register therein discrimination information on the cleaner 3.

After the completion of the above-stated preparation, operation is actually carried out according to the following procedures:

(1) The endoscope 1 which has been examined is attached to the cleaner 3.

(2) The columnar transponder 11 of the endoscope 1 is read (scanned) by the antenna 15 and a scope discrimination signal 41 is fetched into the reader 4.

(3) The nameplate type transponder 12 of the user 5 is scanned by the antenna 15 and the user discrimination signal 42 is fetched into the reader 4.

(4) The nameplate type transponder 13 of the cleaner 3 is scanned by the antenna 15 and the cleaner discrimination signal 43 is fetched into the reader 4.

(5) The cleaner 3 is actuated.

(6) Cleaning information 44 is sequentially transferred to the reader 4 during the operation of the cleaner 3. The cleaning information is data as shown in FIG. 3.

(7) The scope discrimination signal 41, the user discrimination signal 42, the cleaner discrimination signal 43 and the cleaning information 44 which are stored in the reader 4, are transferred to the endoscope information management device 2 simultaneously with the end of the operation of the cleaner 3. Transfer contents may be displayed on the display device 26 before transfer. After checking display contents, a transfer switch (not shown), for example, provided on the reader 4 is depressed to thereby start transfer.

(8) The endoscope information management device 2 updates endoscope management information on the endoscope 1 stored therein. In addition, the peripheral device transmits operation information or the like to the endoscope information management device 2. The transmitted information is processed by and added to the endoscope management information by the endoscope information management device 2. The endoscope information management device 2 also records and updates the respective pieces of information.

(9) The user 5 looks at the information on the endoscope 1, checks, for example, whether or not the endoscope 1 has been already cleaned/disinfected and judges whether or not the endoscope may be used for a test.

(10) Thereafter, a test is conducted.

As stated above, the endoscope information management device 2 obtains the information on the endoscope 1 and that on the peripheral device and creates endoscope management information. Therefore, information such as the cleaning information (cleaner used, cleaning/disinfection date, person who cleaned/disinfected the endoscope, etc.), use history (day when the endoscope was used, cumulative times of use (cleaning/disinfection), users, previous inspection/maintenance day) and the like are automatically managed by the endoscope information management device 2. Accordingly, the user can employ an endoscope the cleaning information on which is clearly displayed on the display device 26, prevent the endoscope from being damaged and definitely know inspection timing.

The cleaning/disinfection information and use history of the endoscope 1 are automatically managed and the user can promptly check the management status. The columnar transponder 11 can be freely attached and detached to/from the endoscope. Due to this, even if the endoscope 1 is damaged, the columnar transponder 11 can be attached to another endoscope 1 and the endoscope can be used.

Further, even if the transponder 11 is damaged, a new transponder may be registered while associating the new transponder with the existing endoscope. Thus, there is no fear that endoscope management information is lost.

Second Embodiment

Next, the second embodiment of the present invention will be described with reference to FIGS. 4 to 6. FIG. 4 is an overall view of an endoscope system in this embodiment. FIG. 5 is a perspective view of a light source device and a video processor. FIG. 6 is a notation view listing data on use of the video processor.

As in the case of the preceding first embodiment, a columnar transponder 11 is attached to an endoscope 1.

A doctor (person who conducts a test) 51 owns a nameplate type transponder 12. If there are plurality of doctors (persons who conducts tests) 51, the doctors 51 own the individual nameplate type transponders 12, respectively. The doctor 51 is supposed to always carry the nameplate type transponder 12 which also serves as a nameplate.

The video processor 36 which is one of peripheral devices, is provided with a nameplate type transponder 13. If there are a plurality of video processors 36, a plurality of nameplate type transponders 13 are attached to the respective video processors 36.

Moreover, an antenna 15 is connected to the reader 4. As shown in FIG. 5, the antenna 15 is fixed to the video processor 36 while protruding toward the front wall of the processor 36 and disposed at a position at which the antenna 15 can communicate with a columnar transponder 11 and the like.

It is noted that the antenna 15 may be provided to be movable and detachable.

The video processor 36 is connected to a reader 4. A monitor 46 is connected to the video processor 36. Further, the reader 4 is connected to an endoscope information management device 2.

Ways to use the columnar transponder 11, the nameplate type transponder 13, the antenna 15 and the reader 4 are almost the same as those described in the preceding first embodiment except that the registration of the video processor 36 is conducted in this embodiment.

Namely, after the completion of preparation for registration, operation is actually conducted according to the following procedures:

(1) The endoscope 1 used for a test is attached to the video processor 36.

(2) After attaching the endoscope 1 to the processor 36 and allowing the reader 4 to conduct read operation, the antenna 15 reads (scans) the columnar transponder 11 of the endoscope 1 and a scope identification signal 41 is fetched into the reader 4.

(3) The nameplate type transponder 12 of the doctor (person who conducts a test) 51 is scanned by the antenna 15 and a doctor discrimination signal 52 is fetched into the reader 4.

(4) The nameplate type transponder 13 of the video processor 36 is scanned by the antenna 15 and processor information 53 is fetched into the reader 4.

It is noted that the nameplate type transponder 13 can be automatically scanned upon actuating the reader 4 if the transponder 13 is positioned adjacent to the antenna 15 as shown in FIG. 5.

(5) The video processor 36 is actuated.

(6) The reader 4 is provided with a data display function. By turning on, for example, a display switch provided on the reader 4, endoscope management information 54 is read from the endoscope information management device 2 and displayed on the monitor 46 by way of the video processor 36.

(7) The doctor (person who conducts a test) 51 and the user 5 look at the information on the endoscope 1, check, for example, whether or not the endoscope 1 has been already cleaned/disinfected, and judge whether or not the endoscope 1 may be used for a test.

(8) Thereafter, a test is conducted.

At this moment, test information 55 is sequentially transferred to the reader 4 during the operation of the video processor 36. The test information 55 is data the contents of which are shown in FIG. 6.

(9) The doctor discrimination signal 52, the scope discrimination signal 41, the processor information 53 and the test information 55 stored in the reader 4 are transferred to the endoscope information management device 2 simultaneously with the end of the operation of the video processor 36.

At this moment, transfer contents may be displayed on the display device 26 prior to transfer. After checking display contents, a transfer switch provided on the reader 4 is, for example, turned on to thereby start transfer.

(10) The endoscope information management device 2 updates the endoscope management information 54 on the endoscope 1 stored therein.

The cleaning/disinfection information on the endoscope 1 can be checked before employing the endoscope 1 and it is, therefore, possible to prevent the endoscope 1 which has not been disinfected yet from being erroneously employed.

Furthermore, information on use of the video processor 36 can be automatically managed and used to judge whether or not it is necessary to inspect the endoscope 1.

Third Embodiment

Next, the third embodiment of the present invention will be described with reference to FIG. 7.

FIG. 7 is a perspective view showing that a light source device 35 and a video processor 36 are contained in a trolley 61 in an endoscope system.

In this embodiment, the above-stated antenna 15 is attached to the front wall of the trolley 61. The remaining constitution is the same as that described in the preceding embodiments.

It is possible for the antenna 15 to communicate with an endoscope 1, the light source device 35, a columnar transponder 11 of the video processor 36, and a nameplate type transponder 12 without moving the antenna 15.

If the light source device 35 and the video processor 36 are provided at higher portions of the trolley 61, it is also possible for the nameplate type transponder 12 of the doctor (person who conducts a test) 51 to communicate without moving the antenna 15.

In addition to the same advantages as those of the first and second embodiments, the third embodiment has an advantage in that communicating operation can be easily carried out.

Fourth Embodiment

Figure 8:
FIG. 8 is a perspective view of a light source device in an endoscope system in the fourth embodiment according to the present invention.

Next, the fourth embodiment of the present invention will be described with reference to FIG. 8. FIG. 8 is a perspective view of a light source device 35 in an endoscope system in this embodiment.

In this embodiment, an antenna 15 is formed into a gate shape, provided on the front wall of the light source device 35 and concentrically arranged with an endoscope connection section 62.

Since the antenna 15 is arranged on the front wall of the light source device 35, it is further ensured that the antenna 15 communicates with the endoscope 1. Further, since the antenna 15 is gate-shaped, the endoscope system can be constituted in a compact fashion. The other advantages are the same as those of the second embodiment.

Fifth Embodiment

The fifth embodiment of the present invention will be described.

In this embodiment, a reader 4 is, for example, integrated into a video processor 36 shown in, for example, FIG. 5.

According to this embodiment, it is not required to discriminate the video processor 36 itself and the antenna 15 can be freely arranged. Due to this, the space saving of the system and the reliability of communication improve. The other advantages are the same as those of the second embodiment.

Sixth Embodiment

Figure 9:
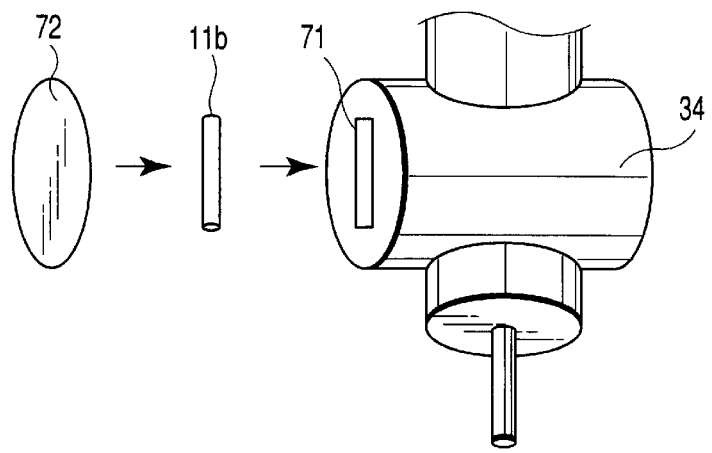
FIG. 9 is a perspective view of a connector section of an endoscope in an endoscope system in the sixth embodiment according to the present invention.
Figure 10:
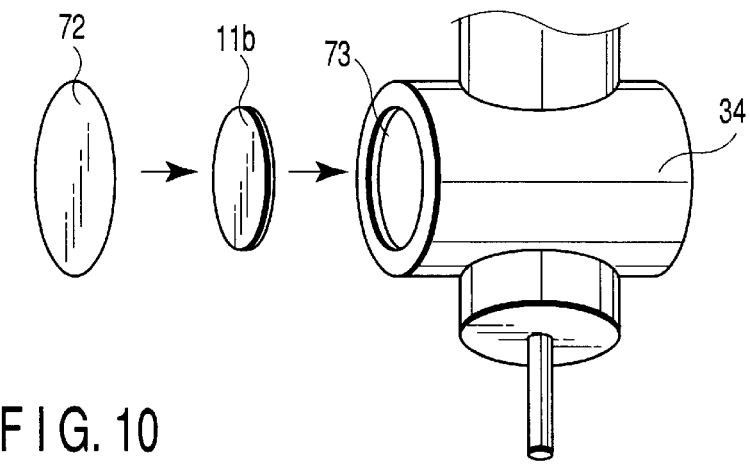
FIG. 10 is a perspective view of another connector section of the endoscope in the endoscope system in the sixth embodiment of an endoscope in the third embodiment according to the present invention.

The sixth embodiment of the present invention will be described with reference to FIGS. 9 and 10. FIGS. 9 and 10 are perspective views of a connector section 34 of an endoscope 1.

FIG. 9 shows that a groove section 71 is provided on the exterior package of the connector section 34 of the endoscope 1 and a columnar transponder 11a is contained in the groove section 71. The groove section 71 has such a shape and a size as to allow the columnar transponder 11 to be tight fitted thereinto. After tight fitting and containing the cylindrical transponder 11 into the groove section 71, the groove section 71 is covered with and closed by a seal 72.

FIG. 10 shows that a disk shaped transponder 11b instead of the cylindrical transponder 11a is employed. Namely, a disk-shaped groove section 73 for fitting thereinto the disk-shaped transponder 11b is provided on the exterior package of the connector section 34 of the endoscope 1 and the disk-shaped transponder 11b is contained in the groove section 73. The groove section 73 containing therein the disk-shaped transponder 11b is covered with and closed by a seal 72. Further, resin out of which the disk-shaped transponder 11b is formed has sufficient durability against chemicals used for cleaning, disinfection and sterilization. For example, the resin may be denatured PPO, fluoroplastic, PSU or silicon.

Since the columnar transponder 11a or the disk-shaped transponder 11b is contained in the groove section 71 or 73 and the groove section 71 or 73 is covered with the seal 72, the columnar transponder 11a or the disk-shaped transponder 11b is not protruded or exposed outside. Due to this, the columnar transponder 11a or the disk-shaped transponder 11b is not an obstacle to handling the endoscope 1 and there is less probability that the transponder 11a or 11b is damaged.

Furthermore, since the columnar transponder 11a or the disk-shaped transponder 11b is provided on the rigid part of the endoscope 1, they do not prevent the movement of the soft part thereof when handing the endoscope 1.

Furthermore, while the transponder 11 made of glass tends to be broken if impact is applied thereto, the strength of the transponder 11 can be intensified by forming the transponder 11 out of resin. Besides, since durability against medicine is ensured, it is possible to prevent the deterioration of the transponder 11. Furthermore, the transponder 11 is molded, the shape thereof can be freely changed.

The other functions and advantages are the same as those in the first and second embodiments.

Seventh Embodiment

Figure 11:
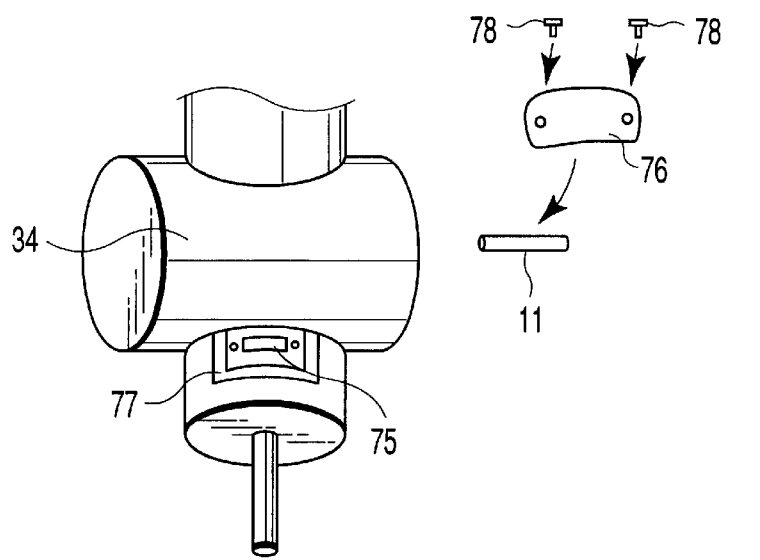
FIG. 11 is a perspective view of another connector section of an endoscope in an endoscope system in the seventh embodiment according to the present invention.

The seventh embodiment of the present invention will be described with reference to FIG. 11. FIG. 11 is a perspective view of a connector section 34 of an endoscope 1.

In this embodiment, a groove section 75 is provided on the exterior package of the connector section 34 of the endoscope 1, and a columnar transponder 11 is contained in the groove section 75. The groove section 75 has such a size as to tight fit the columnar transponder 11 thereinto. The opening portion of the groove section 31 containing therein the columnar transponder 11 is covered with a plate 76. A plate fixing section 77 on which the plate 76 is superimposed is formed on the peripheral edge of the groove section 75. The plate 76 is fixed to the plate fixing section 77 using fixing screws 78.

In this embodiment as well as the preceding embodiments, since the columnar transponder 11 is not protruded toward the outer surface of the endoscope 1, there is less probability that the columnar transponder 11 is an obstacle to the replacement of the transponder 11 by another transponder while handling the endoscope 1 and that the transponder 11 is damaged. The other advantages of this embodiment are the same as those in the first and second embodiments.

It is noted that product name and serial number may be put on the surface of the plate 76 fixedly attached to the plate fixing section 77.

Eighth Embodiment

Figure 12:
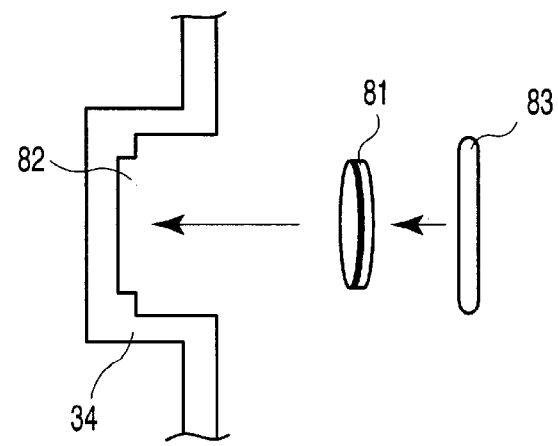
FIG. 12 is a cross-sectional view of a connector section of an endoscope in an endoscope system in the eighth embodiment according to the present invention.

The eighth embodiment of the present invention will be described with reference to FIG. 12. FIG. 12 is a cross-sectional view of an exterior package portion of a connector section 34 of an endoscope 1.

In this embodiment, a groove section 82 having such a size as to be able to contain therein a disk-shaped transponder 81 is provided on the inner wall surface of the exterior package of the connector section 34. This disk-shaped transponder 81 is molded of resin. The disk-shaped transponder 81 is contained in the groove section 82. The groove section 82 is covered with and closed by a seal 83. The disk-shaped transponder 81 is molded of resin.

Since the disk-shaped transponder 81 is provided inside the exterior package of the connector section 34, there is no need to take measures to ensure that the transponder 81 is chemical-proof and the selection range of resin used for the transponder widens. Namely, if resin having good formability is selected, the degree of freedom for the shape of the disk-shaped transponder 81 increases, as well.

It is noted that the transponder to which this embodiment can be applied should not be limited to a disk-shaped transponder.

Ninth Embodiment

Figure 13:
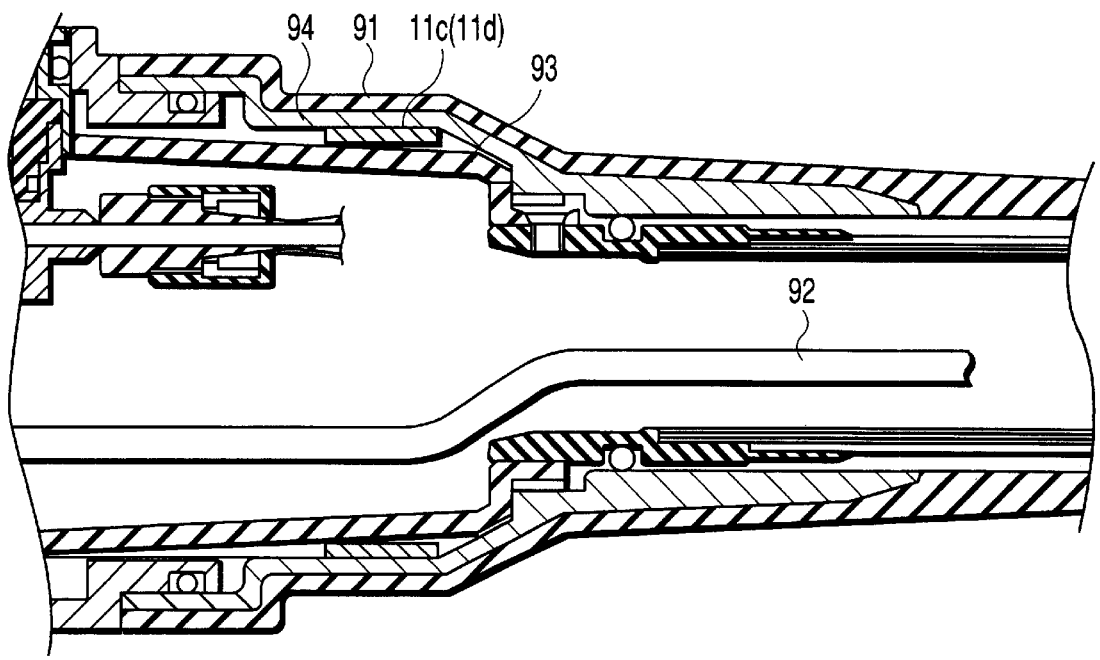
FIG. 13 is a longitudinal sectional view of a folding stopper section of an endoscope in an endoscope system in the ninth embodiment according to the present invention.

The ninth embodiment of the present invention will be described with reference to FIG. 13. FIG. 13 is a longitudinal sectional view of a folding stopper member of an endoscope 1.

In this embodiment, a columnar transponder 11c or a cylindrical transponder 11d is provided in the interior package of the folding stopper member 91 of the endoscope 1. The columnar transponder 11c is formed into a column shape and the cylindrical transponder 11d is formed into a cylinder shape.

A cable 92 for transmitting image signals and the like is disposed on the internal portion of the folding stopper member 91. A shield member 93 for electrically shielding the cable 92 is provided around the cable 92.

As a member for shielding the cable 92, a helical tube or a mesh member as well as a generally cylindrical member such as the shield member 93 may be used.

Further, a cylindrical fixing member 94 for fixing the shield member 93 is positioned on the outer periphery of the shield member 93. The columnar transponder 11c or the cylindrical transponder lid is fixedly provided on the inner surface of the cylindrical fixing member 94.

In this embodiment, since the columnar transponder 11c or the cylindrical transponder 11d is positioned outside of the shield member and the transponder 11c or 11d is electrically shielded, the transponder 11c or 11d does not electromagnetically, adversely affect the endoscope 1 even if it is driven.

Furthermore, if the communication frequency of the columnar transponder 11c or the cylindrical transponder 11d is set in a frequency range in which the frequency does not affect the EMC performance of the endoscope 1, the electromagnetically adverse effect of the transponder on the endoscope 1 is further reduced.

The communication frequency of the columnar transponder 11c or the cylindrical transponder 11d is preferably lower than the drive frequency of the CCD of an electronic endoscope, i.e., 1 MHz or lower, most preferably about 120 to 140 kHz.

Moreover, if the cylindrical transponder 11d is employed, the transponder 11d can be efficiently, surely arranged inside the folding stopper member 91.

The other functions and advantages are the same as those of the preceding first and second embodiments.

Figure 14:
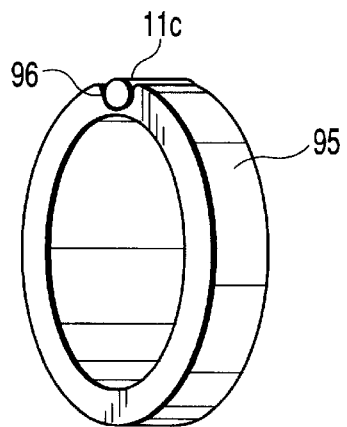
FIG. 14 is a perspective view of an attachment member for a columnar transponder in a modification of the ninth embodiment according to the present invention.

In a modification, a cylindrical fixing member 95 as shown in FIG. 14 is provided on the exterior package of the folding stopper member 91. A groove section 96 is formed in part of the outer periphery of a cylindrical fixing member 95. The cylindrical transponder 11c is disposed within the groove section 96.

Here, the cylindrical fixing member 95 has the same shape as that of the cylindrical transponder 11d stated above and has such a size as to be able to be arranged within the folding stopper member 91. Further, the groove section 96 has such a size as to be able to contain therein the cylindrical transponder 11c. The cylindrical transponder 11c is tight fitted into and fixed to the groove section 96.

According to this modification, even if the cylindrical transponder 11c is employed, the transponder 11c can be surely arranged within the folding stopper member 91. The other functions and advantages are the same as the preceding embodiments.

Tenth Embodiment

In the above-stated second embodiment, the information held by the columnar transponder is CCD information indicating the type of the CCD of the endoscope. Each CCD has a characteristic color tone. If a different CCD is used, it is impossible to make the color tone thereof exactly the same as the previous CCD. A video processor has color tone correction data on the respective CCD's of the endoscope 1.

Further, a reader 4 transmits the CCD information obtained from a columnar transponder to the video processor.

In response to the CCD information, the video processor changes a color tone to be outputted based on the color tone correction data held by the processor.

According to this embodiment, the difference in color tone according to the endoscope 1 (or CCD, in particular) can be corrected and the color tone of a displayed image does not change even if the endoscope 1 is replaced. Accordingly, a user does not need to adjust a color tone.

It is noted that the present invention should not be limited to the above-stated embodiments and that various changes and modifications may be made. For example, the position at which the transponder is attached should not be limited to a position in the vicinity of the connector of the endoscope and may be at the position of the operation section of the endoscope. Further, not only a read-only transponder but also a writable transponder may be employed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an endoscope including a first discrimination section having readable characteristic information about the endoscope;
   a reading section which reads the characteristic information stored in the first discrimination section;
   a cleaner which cleans and/or disinfects the endoscope and sequentially transfers an information item about a cleaning and/or disinfection of the endoscope to the reading section every time said cleaner cleans and/or disinfects the endoscope, said information item including contents of a type of cleaning and/or disinfection that has been conducted by the cleaner; and
   an information management section which manages cleaning and/or disinfection information about the endoscope and a cleaning and/or disinfection history of the endoscope;
   wherein said information management section receives the characteristic information about the endoscope stored in said first discrimination section and the information item about the cleaning and/or disinfection of the endoscope transferred from the reading section and then updates the cleaning and/or disinfection information and the cleaning and/or disinfection history of the endoscope based on the characteristic information of the endoscope by adding the received information item about the cleaning and/or disinfection of the endoscope to the cleaning and/or disinfection information and the cleaning and/or disinfection history of the endoscope.

2. An endoscope system according to claim 1, wherein said first discrimination section comprises an electric wave communication device capable of making non-contact detection.

3. An endoscope system according to claim 1, wherein said first discrimination section is provided detachably to said endoscope.

4. An endoscope system according to claim 1, further comprising a display section which displays said cleaning and/or disinfection information about the endoscope and said cleaning and/or disinfection history of the endoscope.

5. An endoscope system according to claim 1, wherein the characteristic information of the endoscope and the information item for each cleaning and/or disinfection of the endoscope, which are read by the reading section, are transferred to said information management section after finishing of the cleaning and/or disinfection of the endoscope by the cleaner.

6. An endoscope system according to claim 1, further comprising a storage section, which is provided separate from the endoscope, for storing the information items generated by the cleaner.

7. An endoscope system according to claim 1, wherein the information management section comprises a storage section, which is provided separate from the endoscope, for storing the information items generated by the cleaner.

8. An endoscope system comprising:
   an endoscope including a first discrimination section having readable characteristic information about the endoscope;
   a reading section which reads the characteristic information stored in the first discrimination section;
   a cleaner which cleans the endoscope and sequentially transfers an information item about a cleaning of the endoscope to the reading section every time said cleaner cleans the endoscope;
   a cleaning information management section which manages cleaning information about the endoscope and a cleaning history of the endoscope; and
   a video processor which includes a second discrimination section having readable characteristic information about the video processor and which transfers an information item about a use of the endoscope to the reading section every time the endoscope is used to perform a test;
   wherein said cleaning information management section receives the characteristic information about the endoscope stored in said first discrimination section and the information item about the cleaning of the endoscope transferred from the reading section and then updates the cleaning information and the cleaning history of the endoscope based on the characteristic information of the endoscope by adding the received information item about the cleaning of the endoscope to the cleaning information and the cleaning history of the endoscope;
   wherein said reading section reads the characteristic information of the video processor stored in the second discrimination section; and
   wherein said cleaning information management section further manages usage information about usage of the endoscope and a usage history of the endoscope by receiving the characteristic information about the video processor stored in the second discrimination section and the information about the use of the endoscope transferred from the reading section and then updating the usage information and the usage history of the endoscope based on the characteristic information of the video processor by adding the received information item about the use of the endoscope to the usage information and the usage history of the endoscope.

9. An endoscope system comprising:

an endoscope including a first discrimination section having readable characteristic information about the endoscope;

a reading section which reads the characteristic information stored in the first discrimination section;

a cleaner which cleans and/or disinfects the endoscope and sequentially transfers an information item about a cleaning and/or disinfection of the endoscope to the reading section every time said cleaner cleans and/or disinfects the endoscope, said information item including contents of a type of cleaning and/or disinfection that has been conducted by the cleaner;

an information management section which manages cleaning and/or disinfection information about the endoscope and a cleaning and/or disinfection history of the endoscope; and a third discrimination section that identifies an operator of the endoscope;

wherein said information management section receives the characteristic information about the endoscope stored in said first discrimination section and the information item about the cleaning and/or disinfection of the endoscope transferred from the reading section and then updates the cleaning and/or disinfection information and the cleaning and/or disinfection history of the endoscope based on the characteristic information of the endoscope by adding the received information item about the cleaning and/or disinfection of the endoscope to the cleaning and/or disinfection information and the cleaning and/or disinfection history of the endoscope;

wherein said reading section reads operator information stored in the third discrimination section; and wherein said information management section manages said cleaning and/or disinfection information and said cleaning and/or disinfection history of the endoscope in association with the operator information read by the reading section.

10. An endoscope system comprising:

an endoscope including an endoscope discrimination section having readable characteristic information about the endoscope;

a cleaner which cleans and/or disinfects the endoscope and which includes a cleaner discrimination section having readable characteristic information about the cleaner;

a reading section which reads the characteristic information stored in the endoscope discrimination section and the characteristic information stored in the cleaner discrimination section, and which also reads an information item about a cleaning and/or disinfection of the endoscope every time said cleaner cleans and/or disinfects the endoscope, said information item including contents of a type of cleaning and/or disinfection that has been conducted by the cleaner; and a management section which receives the characteristic information about the endoscope and the characteristic information about cleaner and the information item about the cleaning and/or disinfection of the endoscope read by the reading section, and which manages cleaning and/or disinfection information and a cleaning and/or disinfection history of the endoscope;

wherein the management section associates the characteristic information about the endoscope and the characteristic information about the cleaner read by the reading section with the information item about the cleaning and/or disinfection information read by the reading section each time cleaning and/or disinfection is carried out by the cleaner, and updates the cleaning and/or disinfection information and the cleaning and/or disinfection history by adding the read information item to the cleaning and/or disinfection information and the cleaning and/or disinfection history of the endoscope each time cleaning and/or disinfection is carried out by the cleaner.

11. An endoscope system according to claim 10, further comprising:

an operator discriminating section having identification information that identifies an operator of the endoscope;

wherein the reading section also reads the identification information of the operator stored in the operator discriminating section; and wherein the management section also associates the read identification information of the operator with a use history of the endoscope, and manages the cleaning and/or disinfection information and the cleaning and/or disinfection history of the endoscope in accordance with the read identification information and the use history of the endoscope.

12. An endoscope system according to claim 11, wherein the characteristic information about the endoscope and the information item for each cleaning and/or disinfection of the endoscope, which are read by the reading section, are transferred to the management section after finishing of the cleaning and/or disinfection of the endoscope by the cleaner.

13. An endoscope system according to claim 11, further comprising:

a display section which displays information managed by the management section; and a video processor including a video processor identification section having characteristic information about the video processor;

wherein the management section displays whether or not the cleaning and/or disinfection of the endoscope is finished, based on the characteristic information about the endoscope stored in the endoscope identification section and the cleaning and/or disinfection information and the cleaning and/or disinfection history of the endoscope stored in the management section.

14. An endoscope system according to claim 11, further comprising:

a display section which displays information managed by the management section; and a video processor including a video processor identification section having characteristic information about the video processor;

wherein the reading section also reads the characteristic information about the video processor stored in the video processor identification section, and use information of the video processor each time the video processor is used; and wherein the management section also associates the characteristic information about the video processor and the use information thereof with the characteristic information about the endoscope and the characteristic information about the cleaner, and manages the cleaning and/or disinfection information and the cleaning and/or disinfection history of the endoscope in accordance with the characteristic information about the video processor and the use information thereof.

15. An endoscope system according to claim 14, wherein the characteristic information of the video processor and the use information thereof, which are read by the reading section, are transferred to the management section after operation of the video processor is finished.

* * * * *